(12) United States Patent
Iguchi et al.

(10) Patent No.: US 8,643,839 B2
(45) Date of Patent: Feb. 4, 2014

(54) SPECTROMETER

(75) Inventors: Kazuya Iguchi, Hamamatsu (JP); Kengo Suzuki, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 328 days.

(21) Appl. No.: 13/131,777

(22) PCT Filed: Sep. 24, 2009

(86) PCT No.: PCT/JP2009/066544
§ 371 (c)(1),
(2), (4) Date: May 27, 2011

(87) PCT Pub. No.: WO2010/073785
PCT Pub. Date: Jul. 1, 2010

(65) Prior Publication Data
US 2011/0235035 A1    Sep. 29, 2011

(30) Foreign Application Priority Data

Dec. 24, 2008    (JP) ................................. 2008-327852

(51) Int. Cl.
*G01J 3/28*    (2006.01)
*G01J 1/46*    (2006.01)
(52) U.S. Cl.
USPC ......................................... 356/326; 356/215
(58) Field of Classification Search
USPC ............................. 356/215, 236, 326; 250/228
See application file for complete search history.

(56) References Cited

U.S. PATENT DOCUMENTS 3,874,799 A     4/1975  Isaacs et al.
4,572,668 A *   2/1986  Auth ............................ 356/318

(Continued)

FOREIGN PATENT DOCUMENTS

CN     86 1 06696     4/1987
GB      2181268       4/1987

(Continued)

OTHER PUBLICATIONS

Bowen et al., The Effect of Temperature on Fluorescence of Solutions, J. Phys. Chem, 1959, 63(1), pp. 4-7.*

(Continued)

*Primary Examiner* — Gregory J Toatley
*Assistant Examiner* — Shawn Decenzo
(74) *Attorney, Agent, or Firm* — Drinker Biddle & Reath LLP

(57) ABSTRACT

A spectrometer is provided with an integrating sphere 20, inside which a sample S of a measurement target is disposed and which is adapted for observing measured light emitted from the sample S, and a Dewar vessel 50 which retains a refrigerant R for cooling the sample S and at least a portion of which is located so as to face the interior of the integrating sphere 20. Gas generated from the refrigerant R is introduced through predetermined gaps G1-G6 functioning as a gas introduction path and through a plurality of communicating passages 64 formed in a support pedestal 61, into the integrating sphere 20. The gas introduced into the integrating sphere 20 absorbs water in the integrating sphere 20 to decrease the temperature in the integrating sphere 20, so as to prevent dew condensation from occurring on a portion of a second container portion 50b of the Dewar vessel 50 exposed in the integrating sphere 20. This can prevent occurrence of dew condensation even in the case where the sample S is measured in a cooled state at a desired temperature.

19 Claims, 14 Drawing Sheets

(56) References Cited

U.S. PATENT DOCUMENTS

| | | | |
|---|---|---|---|
| 4,746,214 A * | 5/1988 | Akiyama et al. | 356/325 |
| 4,990,782 A | 2/1991 | Wellman et al. | |
| 5,098,195 A | 3/1992 | Halyo et al. | |
| 5,258,363 A * | 11/1993 | Hed | 505/160 |
| 5,471,053 A | 11/1995 | Diner et al. | |
| 5,517,315 A | 5/1996 | Snail et al. | |
| 5,745,234 A | 4/1998 | Snail et al. | |
| 6,147,350 A | 11/2000 | Beecroft et al. | |
| 7,339,665 B2 | 3/2008 | Imura | |
| 7,508,503 B2 * | 3/2009 | Jang | 356/236 |
| 7,869,049 B2 | 1/2011 | Baba et al. | |
| 8,324,561 B2 * | 12/2012 | Iguchi et al. | 250/228 |
| 2008/0204705 A1 | 8/2008 | Liu | |

FOREIGN PATENT DOCUMENTS

| | | |
|---|---|---|
| JP | 54-35114 | 10/1979 |
| JP | 61-82442 | 4/1986 |
| JP | 2-236453 | 9/1990 |
| JP | 3-268443 | 11/1991 |
| JP | 6-201585 | 7/1994 |
| JP | 7-146175 | 6/1995 |
| JP | 11-173982 | 7/1999 |
| JP | 2001-59812 | 3/2001 |
| JP | 2003-215041 | 7/2003 |
| JP | 2005-140546 | 6/2005 |
| JP | 2007-33334 | 2/2007 |
| JP | 2007-86031 | 4/2007 |
| JP | 2007-198983 | 8/2007 |
| JP | 2009-31015 | 2/2009 |
| JP | 2009-31016 | 2/2009 |
| JP | 2009-74866 | 4/2009 |
| WO | 2007/007947 | 1/2007 |

OTHER PUBLICATIONS

M. Thiede et al., "In situ UV/Vis/near-IR diffuse reflection measurement of catalysts at temperature up to 673 K," Review of Scientific Instruments, Feb. 2002, pp. 394-397, vol. 73, No. 2, American Institute of Physics.

Kazuhiko Kioke, et al, "A simple integrating-sphere fluorometer for monitoring the growth of benthic microalgae," La mer 32, 1994, pp. 45-50.

G. Palmer et al., "Diffuse Reflectance Spectroscopy of Frozen Samples as an Adjunct to Low-Temperature Electron Paramagnetic Resonance Spectroscopy," Analytical Biochemistry, vol. 8, No. 1, May 1, 1964, pp. 95-103, XP024817418.

K. Klier et al., "Spectra of Zynthetic Zeolites Containing Transition Metal Ions—II. $Ni^{2+}$ Ions in Type A Linde Molecular Sieves," Journal of Physics and Chemistry of Solids, vol. 29, No. 6, Jun. 1, 1968, pp. 951-957, XP024582194.

W. Chung-Chih et al., "Hole-Transport Properties of a Furan-Containing Oligoaryl," Journal of Applied Physics, vol. 93, No. 9, May 1, 2003, pp. 5465-5471, XP012059556.

L. S. Slobodkin et al., "Near Infrared Reflection Spectra of Ammonia Frost: Interpretation of The Upper Clouds of Saturn," Journal of Quantitative Spectroscopy and Radiative Transfer, vol. 20, No. 5, Nov. 1, 1978, pp. 481-490, XP024424975.

\* cited by examiner

SPECTROMETER

TECHNICAL FIELD

The present invention relates to a spectrometer provided with an integrating sphere and adapted for measuring a sample cooled at a desired temperature.

BACKGROUND ART

There is a known spectrometer which is provided with an integrating sphere for observing measured light emitted from a sample and which is configured to cool the sample (e.g., cf. Patent Literature 1). In the spectrometer described in Patent Literature 1, the sample is cooled at a desired temperature by bringing the sample, which is arranged to face the interior of the integrating sphere, into contact with a refrigerant.

There is another known spectrometer provided with an integrating sphere and adapted for cooling the interior of the integrating sphere (e.g., cf. Patent Literature 2). In the spectrometer described in Patent Literature 2, cold air is introduced into the integrating sphere to cool the integrating sphere at a desired temperature.

Applicants filed applications entitled a light detecting apparatus provided with an integrating sphere (e.g., cf. Patent Literature 3).

CITATION LIST

Patent Literature

Patent Literature 1: Japanese Patent Application Laid-open No. S61-082442
Patent Literature 2: Japanese Patent Application Laid-open No. H07-146175
Patent Literature 3: Japanese Patent Application Laid-open No. 2007-86031

SUMMARY OF INVENTION

Technical Problem

In the spectrometer described in Patent Literature 1, the sample is cooled by bringing the sample into contact with the refrigerant. For this reason, water condenses on a portion of the sample exposed in the integrating sphere, to impede appropriate measurement. The dew condensation on the sample hinders incidence of the measured light into the sample or the like. An internal peripheral surface of the integrating sphere is generally made of a diffuse reflective material with high reflectance and with excellent diffuse capability (e.g., Spectralon (registered trademark), barium sulfate, and so on). Depending upon an ingredient of the diffuse reflective material, the diffuse reflective material will dissolve with attachment of the condensed water, so as to make diffuse reflection insufficient on the internal peripheral surface of the integrating sphere.

In the spectrometer described in Patent Literature 2, cold air is introduced into the integrating sphere to cool the integrating sphere, which is for absorbing heat generated from a lamp disposed in the integrating sphere; therefore, nothing is considered about cooling of the sample. Since a measurement target is the lamp to radiate heat, the aforementioned problem of dew condensation cannot arise.

Incidentally, it is conceivable to use a Dewar vessel retaining a refrigerant, in order to easily and efficiently cool the sample. However, even in the case where the Dewar vessel is used, it is difficult to prevent the dew condensation on a portion of the Dewar vessel exposed in the integrating sphere.

It is an object of the present invention to provide a spectrometer capable of preventing occurrence of dew condensation even in the case where a sample is measured in a cooled state at a desired temperature.

Solution to Problem

The present invention provides a spectrometer comprising an integrating sphere inside which a sample of a measurement target is disposed and which is adapted for observing measured light emitted from the sample, the spectrometer comprising: a Dewar vessel which retains a refrigerant for cooling the sample and at least a portion of which is located so as to face the interior of the integrating sphere; and a gas introduction path which introduces gas generated from the refrigerant retained in the Dewar vessel, into the integrating sphere.

In the present invention, the refrigerant retained in the Dewar vessel evaporates to generate dry gas at a relatively low temperature. The gas generated from the refrigerant is introduced through the gas introduction path into the integrating sphere. For this reason, the interior of the integrating sphere is kept in a relatively cool and dry ambience by the gas generated from the refrigerant, so as to prevent occurrence of dew condensation on the portion of the Dewar vessel exposed in the integrating sphere.

Preferably, the spectrometer further comprises a cover which covers a portion of the Dewar vessel exposed out of the integrating sphere. In this case, while the gas generated from the refrigerant is prevented from being discharged to the outside of the apparatus, the gas can be efficiently introduced into the integrating sphere.

More preferably, the cover is provided with the gas introduction path. In this case, installation of the gas introduction path can be implemented in a secure and easy manner.

Preferably, the spectrometer further comprises a sample holder which houses the sample and which is disposed in the Dewar vessel. In this case, the sample can be cooled by the refrigerant, without contact therewith.

Preferably, the spectrometer further comprises a gas introduction path which introduces dry gas into the integrating sphere. In this case, it becomes feasible to further prevent the dew condensation from occurring on the portion of the Dewar vessel exposed in the integrating sphere.

Advantageous Effects of Invention

The present invention provides the spectrometer capable of preventing occurrence of dew condensation even in the case where the sample is measured in the cooled state at a desired temperature.

DESCRIPTION OF EMBODIMENTS

Preferred embodiments of the present invention will be described below in detail with reference to the accompanying drawings. In the description, the same elements or elements with the same functionality will be denoted by the same reference signs, without redundant description.

Figure 1:
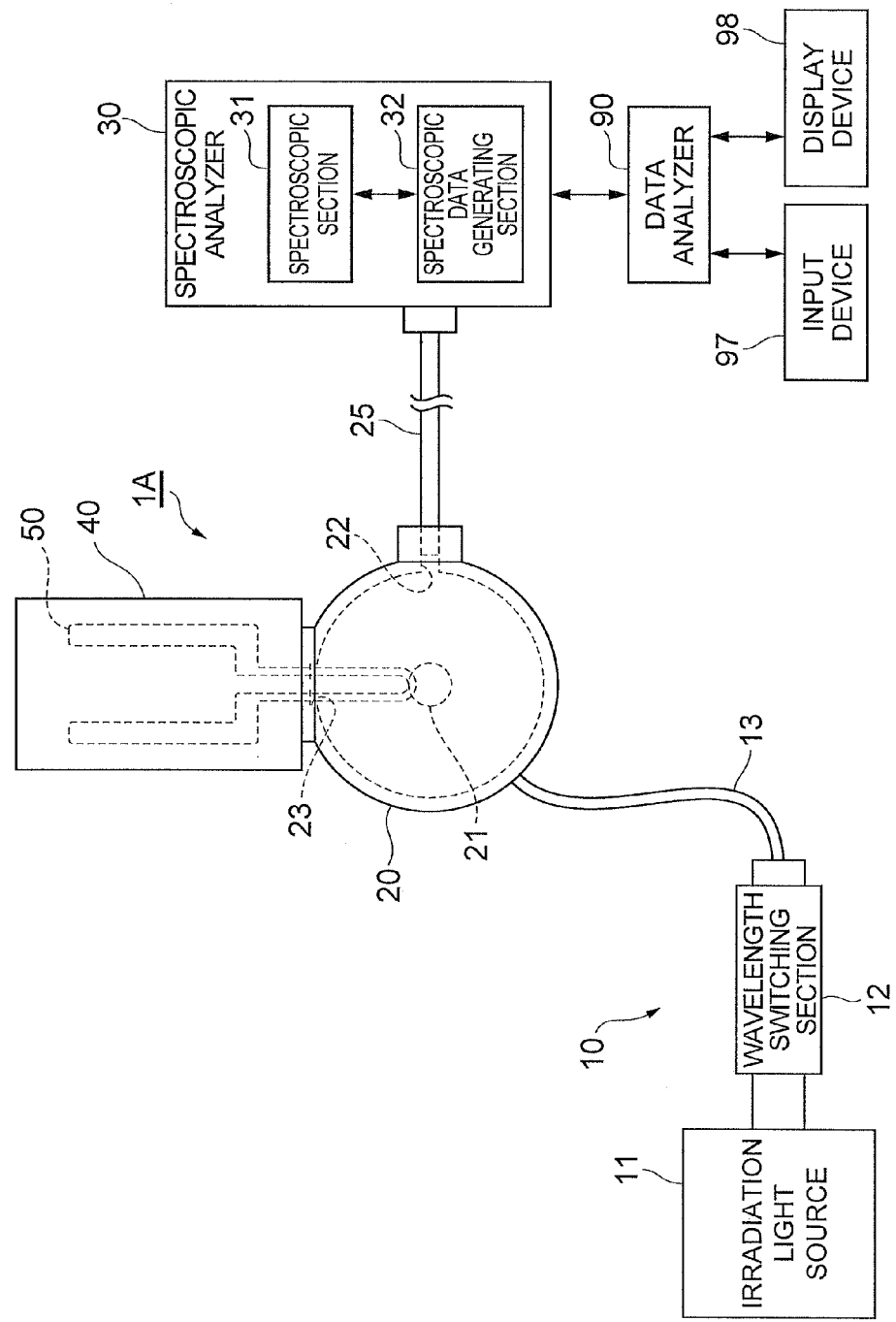
FIG. 1 is a drawing schematically showing a configuration of an embodiment of the spectrometer.

FIG. 1 is a drawing schematically showing a configuration of a spectrometer according to an embodiment of the present invention. The spectrometer 1A of the present embodiment is provided with an irradiation light supplying section 10, an integrating sphere 20, a spectroscopic analyzer 30, a Dewar housing 40, a Dewar vessel 50, and a data analyzer 90. The spectrometer 1A is configured to irradiate a sample S such as a luminescence material with excitation light of a predetermined wavelength and to enable measurement and evaluation of luminescence properties such as a fluorescence property of the sample S by the photoluminescence (PL) method.

The irradiation light supplying section 10 supplies the excitation light for measurement of the luminescence properties of the sample S, as irradiation light supplied into the interior of the integrating sphere 20 housing the sample S of a measurement target. The irradiation light supplying section 10 functions as an irradiation light supplying means. In FIG. 1, the irradiation light supplying section 10 is composed of an irradiation light source 11, and a light guide 13 which guides the light from the irradiation light source 11 to the integrating sphere 20. In the irradiation light supplying section 10, a wavelength switching section 12 is set up between the irradiation light source 11 and the light guide 13. In this setup, the irradiation light supplying section 10 is configured to enable switch between the excitation light of the predetermined wavelength and light consisting of light components in a predetermined wavelength range (which will be referred to as white light). Therefore, the irradiation light supplying section 10 functions as an excitation light supplying means and white light supplying means.

A specific configuration example of the irradiation light supplying section 10 applicable herein is a configuration using a white light source as the irradiation light source 11 and providing the wavelength switching section 12 with a wavelength selection means to select only a light component in the predetermined wavelength range out of the light supplied from the irradiation light source 11 and to let the light component pass through the light guide 13. In this case, when the wavelength switching section 12 turns wavelength selection OFF, the irradiation light into the integrating sphere 20 is white light; when the wavelength switching section 12 turns wavelength selection ON, the irradiation light into the integrating sphere 20 is the excitation light of the predetermined wavelength. Specifically, the wavelength selection means applicable herein is, for example, a spectroscopic filter, a spectroscope, or the like.

The integrating sphere 20 is used in measurement of the luminescence properties of the sample S disposed inside. The integrating sphere 20 is configured with an entrance aperture 21 for inputting the excitation light with which the sample S is irradiated into the integrating sphere 20, an exit aperture 22 for outputting measured light from the sample S to the outside, and a first sample introduction opening 23 for introducing the sample S into the interior of the integrating sphere 20. The Dewar housing 40 is detachably fitted in the first sample introduction opening 23 with attachment screws.

An exit end of the light guide 13 for inputting of irradiation light is fixed to the entrance aperture 21 of the integrating sphere 20. The light guide 13 applicable herein is, for example, an optical fiber. An entrance end of a light guide 25 for guiding the measured light from the sample S to the latter-stage spectroscopic analyzer 30 is fixed to the exit aperture 22 of the integrating sphere 20. The light guide 25 applicable herein is, for example, a single fiber or a bundle fiber.

The spectroscopic analyzer 30 disperses the measured light from the sample S output from the exit aperture 22 of the integrating sphere 20 through the light guide 25, to obtain a wavelength spectrum thereof. The spectroscopic analyzer 30 functions as a dispersing means. In the present configuration example, the spectroscopic analyzer 30 is configured as a photonic multichannel analyzer having a spectroscopic section 31 and a spectroscopic data generating section 32.

The spectroscopic section 31 is composed of a spectrometer for resolving the measured light into wavelength components, and a photodetector for detecting light from the spectrometer. The photodetector applicable herein is, for example, a CCD linear sensor consisting of a one-dimensional array of pixels of multiple channels (e.g., 1024 channels) for detecting respective spectrally-resolved wavelength components of the measured light. A measured wavelength region by the spectroscopic section 31 may be optionally set according to a specific configuration and others and is, for example, from 300 nm to 950 nm. The spectroscopic data generating section 32 performs required signal processing for detection signals output from the respective channels of the photodetector of the spectroscopic section 31, to generate data of a wavelength spectrum being spectroscopic data of the measured light. The spectroscopic data generating section 32 functions as a spectroscopic data generating means. The data of the wavelength spectrum generated and obtained by the spectroscopic data generating section 32 is output to the latter-stage data analyzer 90.

The data analyzer 90 is a data analyzing means which performs a data analysis necessary for the wavelength spectrum obtained by the spectroscopic analyzer 30, to obtain information about the sample S. The specific content of the data analysis in the data analyzer 90 will be described later.

Connected to the data analyzer 90 are an input device 97 used for input of instructions about the data analysis and others, input of analysis conditions, and so on, and a display device 98 used for display of the data analysis result and others.

Figure 2:
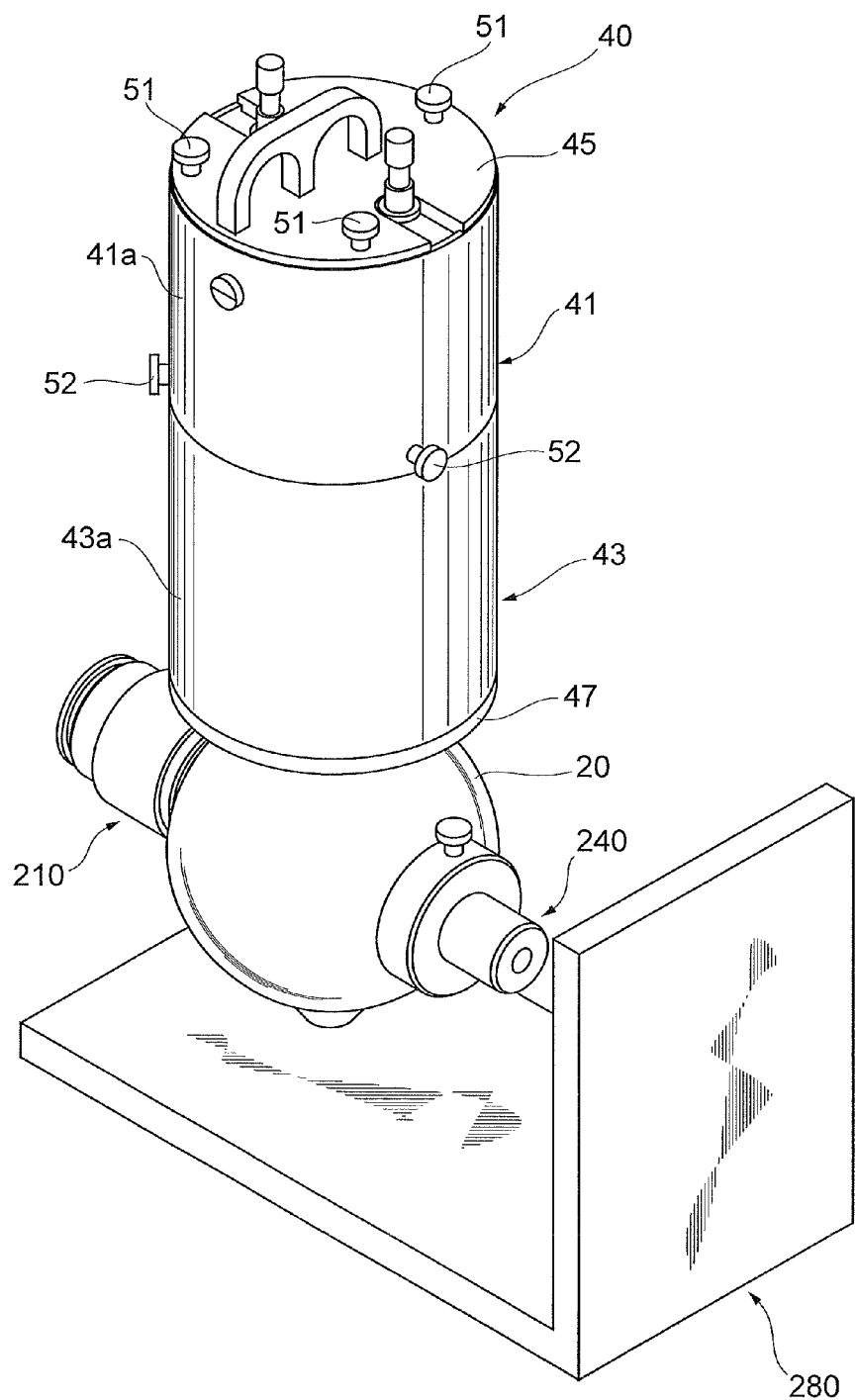
FIG. 2 is a perspective view showing an example of configurations of an integrating sphere and a Dewar housing.
Figure 3:
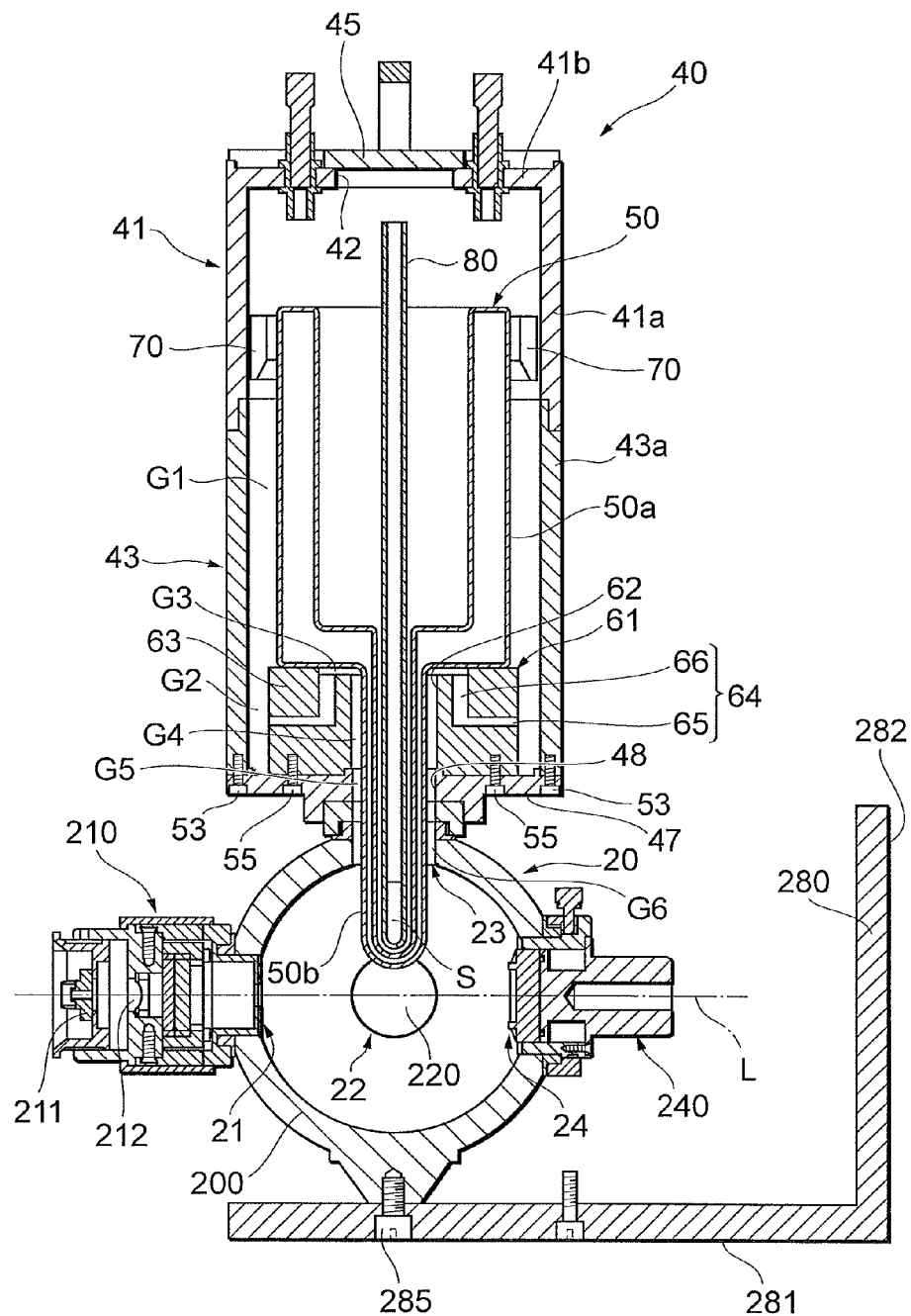
FIG. 3 is a sectional view showing an example of configurations of the integrating sphere, Dewar housing, and Dewar vessel.
Figure 4:
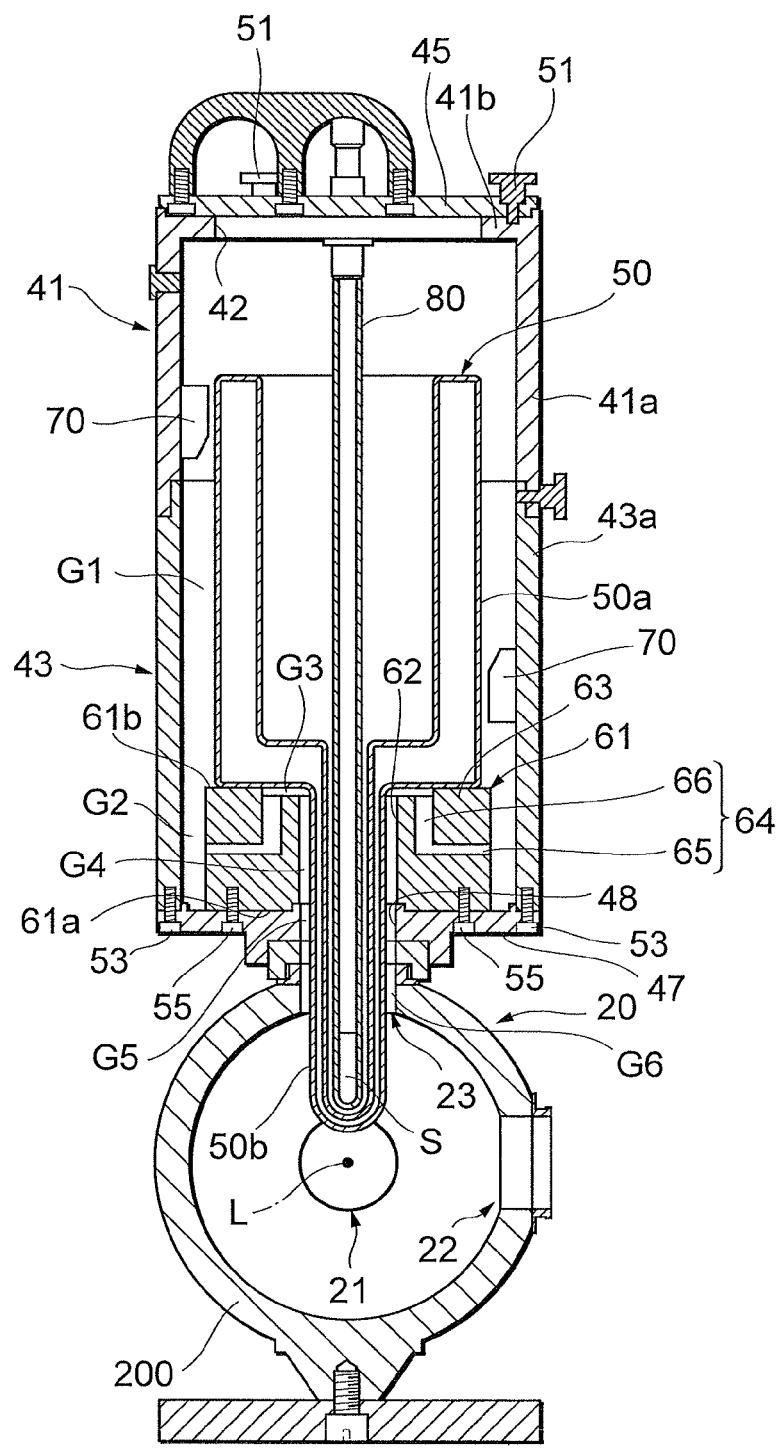
FIG. 4 is a sectional view showing an example of configurations of the integrating sphere, Dewar housing, and Dewar vessel.
Figure 5:
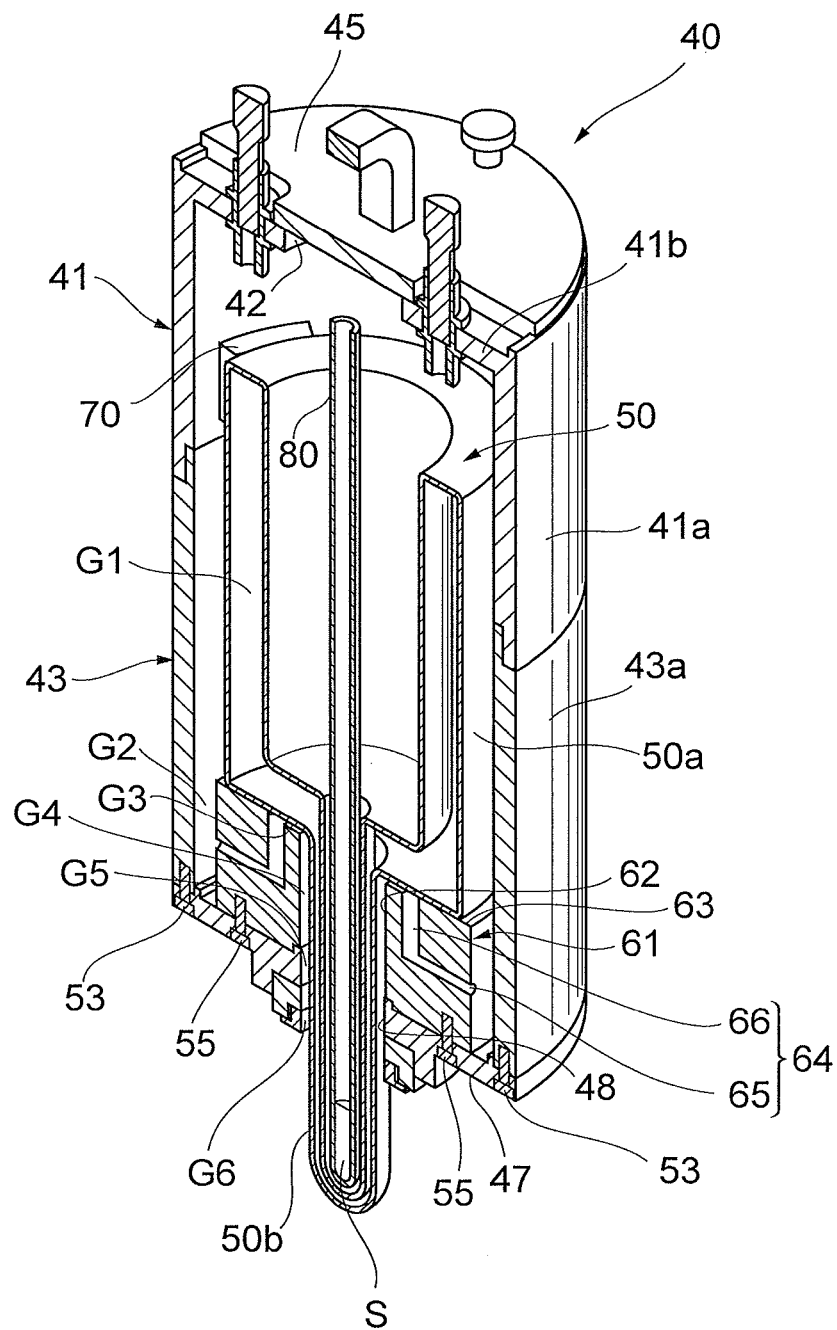
FIG. 5 is a sectional view showing an example of configurations of the integrating sphere, Dewar housing, and Dewar vessel.
Figure 6:
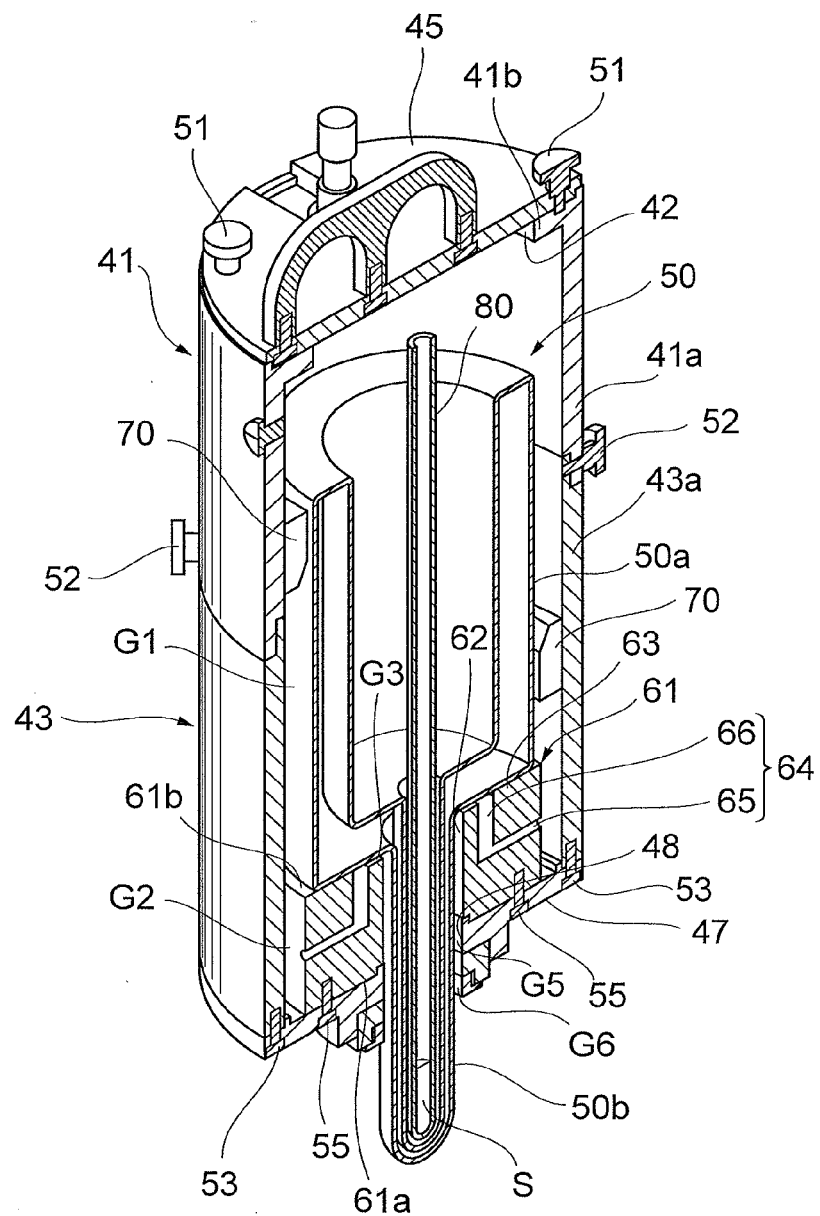
FIG. 6 is a sectional view showing an example of configurations of the integrating sphere, Dewar housing, and Dewar vessel.
Figure 7:
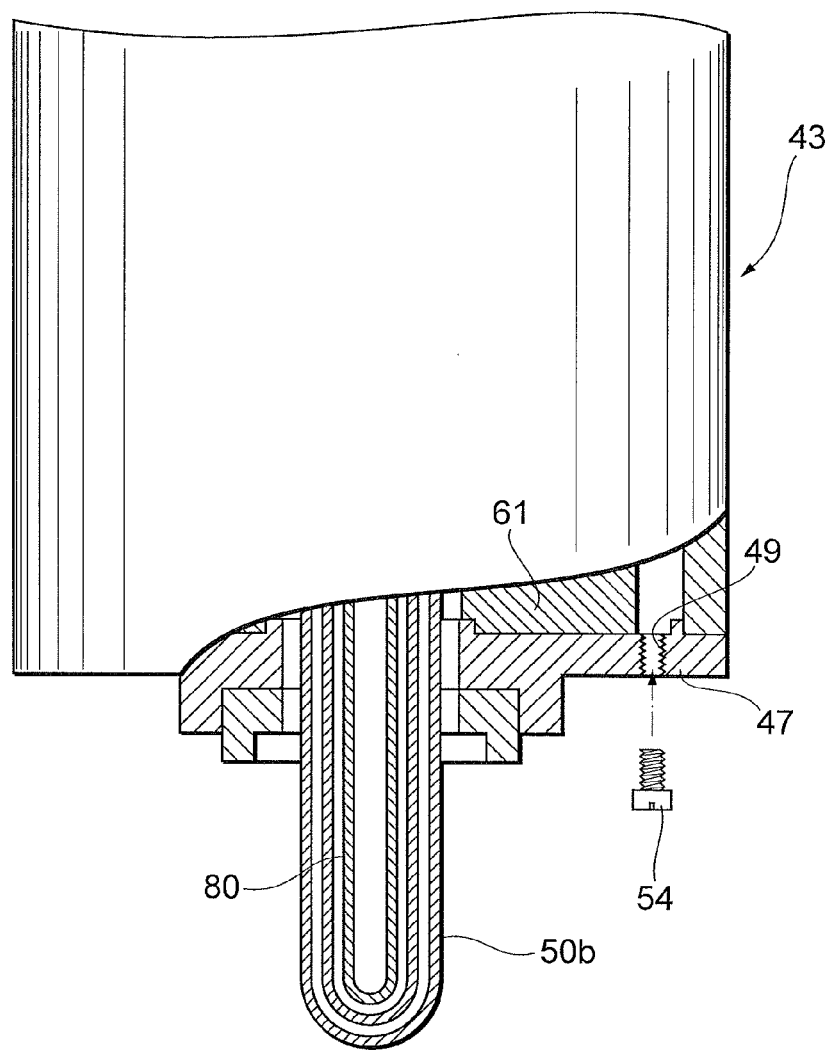
FIG. 7 is a sectional view showing an example of a configuration of a drainage opening.

The following will describe configurations of the integrating sphere 20, Dewar housing 40, and Dewar vessel 50 used in the spectrometer 1A shown in FIG. 1, with reference to FIGS. 2 to 6. FIG. 2 is a perspective view showing an example of the configurations of the integrating sphere 20 and Dewar housing 40 used in the spectrometer 1A shown in FIG. 1. FIGS. 3 to 6 are sectional views showing an example of the configurations of the integrating sphere 20, Dewar housing 40, and Dewar vessel 50 and show the configurations of the integrating sphere 20, Dewar housing 40, and Dewar vessel 50 in cross sections along the irradiation optical axis L of the excitation light. The cross sections in FIGS. 3 and 5 and the cross sections in FIGS. 4 and 6 are perpendicular to each other.

The integrating sphere 20 is provided with an integrating sphere body 200 attached to a mount 280 with an attachment screw 285. The mount 280 is formed in an L-shape with two ground contact surfaces 281, 282 perpendicular to each other. The irradiation optical axis L extends in a direction parallel to the ground contact surface 281 and perpendicular to the ground contact surface 282, while passing the center position of the integrating sphere body. 200.

The integrating sphere body 200 is provided with the entrance aperture 21, exit aperture 22, and first sample introduction opening 23 shown in FIG. 1. The entrance aperture 21 is provided at a predetermined position of the integrating sphere body 200 on one end side of the optical axis L (i.e., at a left position in the drawing). The exit aperture 22 is provided at a predetermined position on a surface passing the center position of the integrating sphere body 200 and being perpendicular to the optical axis L. The first sample introduction opening 23 is provided at a position of a 90° shift (upper position in the drawing) from the exit aperture 22 when viewed from the center position on the surface passing the center position of the integrating sphere body 200 and being perpendicular to the optical axis L.

In the configuration example shown in FIG. 3, a second sample introduction opening 24 is provided in addition to the first sample introduction opening 23. The second sample introduction opening 24 is provided at a position opposed to the entrance aperture 21 on the other end side of the optical axis L (i.e., at a right position in the drawing). The second sample introduction opening 24 is fitted with a sample holder 240 for mounting of a sample.

A light guide holder 210 for connection of the light guide 13 for inputting of irradiation light is inserted and fitted in the entrance aperture 21. A light guide holder 220 for connection of the light guide 25 for emission of measured light is inserted and fitted in the exit aperture 22. FIGS. 2 to 6 are drawn without illustration of the light guides 13, 25.

Provided in the Dewar housing 40 are a sample holder 80 which holds the sample S at a predetermined position in the integrating sphere 20, and the Dewar vessel 50 for cooling the sample S held in the sample holder 80. The sample holder 80 is a tubular member closed at one end. The Dewar vessel 50 is for retaining a refrigerant (e.g., liquid nitrogen or the like) to cool the sample S and is a nearly tubular container closed at one end. The Dewar vessel 50 is constructed in a heat-insulated double structure with a vacuum layer. The sample holder 80 is arranged as positioned inside the Dewar vessel 50. The Dewar vessel 50 has a first container portion 50a having a first inside diameter and located on the other end side, and a second container portion 50b having a second inside diameter smaller than the first inside diameter and located on one end side.

The second inside diameter is set larger than the outside diameter of the sample holder 80 and, in a state in which the sample holder 80 is disposed in the Dewar vessel 50, a space is created between the second container portion 50b and the sample holder 80. As the refrigerant is present in the space between the second container portion 50b and the sample holder 80, the sample S held on one end side of the sample holder 80 is cooled.

The Dewar housing 40 is a member having a space for housing the Dewar vessel 50 inside, and has a first case 41, a second case 43, a first lid plate 45, and a second lid plate 47. The first case 41 consists of a cylinder portion 41a of a tubular shape (cylindrical shape in the present embodiment) and a bottom portion 41b located on one end side of the cylinder portion 41a, and is a member with a bottom. The bottom portion 41b has an opening 42 formed in a central region thereof. The first lid plate 45 is detachably attached to the bottom portion 41b of the first case 41 with attachment screws 51, to close the opening 42 formed in the bottom portion 41b.

The second case 43 consists of a cylinder portion 43a of a tubular shape (cylindrical shape in the present embodiment) opening at both ends. The first case 41 and second case 43 are detachably attached to each other with attachment screws 52 and fixed in a state in which their respective other ends are in contact with each other. The second lid plate 47 is detachably attached to one end of the second case 43 with attachment screws 53 to close an opening at the one end. An opening 48 for insertion of the second container portion 50b of the Dewar vessel 50 is formed in a central region of the second lid plate 47 so as to communicate with the first sample introduction opening 23. Formed in the second lid plate 47 is a drainage opening 49 for drainage of water collected in the Dewar housing 40. The drainage opening 49 is usually closed by a screw 54.

The Dewar vessel 50 is radially positioned by a plurality of spacers 70 disposed at predetermined intervals on internal peripheral surfaces of the first case 41 and the second case 43. The spacers 70 form a predetermined gap G1 between the internal peripheral surfaces of the first case 41 and the second case 43 and the external peripheral surface of the first container portion 50a of the Dewar vessel 50.

A support pedestal 61 supporting the Dewar vessel 50 is detachably attached to the second lid plate 47 with attachment screws 55. The support pedestal 61 is a nearly columnar member. A through hole 62 for insertion of the second container portion 50b of the Dewar vessel 50 is formed in a central portion of the support pedestal 61 so as to communicate with the opening 48 formed in the second lid plate 47. A predetermined gap G2 is formed between the internal peripheral surface of the second case 43 and the external peripheral surface of the support pedestal 61. An annular packing (not shown) is provided so as to surround the through hole 62, between the second lid plate 47 and the support pedestal 61. As this packing is interposed between the second lid plate 47 and the support pedestal 61, water-tightness is achieved between the second lid plate 47 and the support pedestal 61.

The support pedestal 61 is provided with a projecting portion 63 projecting from a second surface 61b, on the second surface 61b opposed to a first surface 61a attached to the second lid plate 47 so as to contact it. The projecting portion 63 is formed in a ring shape, when viewed from the center axis direction of the through hole 62, so as to surround the outside of the through hole 62. The projecting portion 63 is in contact with the Dewar vessel 50 to define the position of the Dewar vessel 50 in an insertion direction thereof. The second surface 61b of the support pedestal 61 and the Dewar vessel 50 are separated by a distance of a height of the projecting portion 63 to form a predetermined gap G3 between the second surface 61b of the support pedestal 61 and the Dewar vessel 50. An annular packing (not shown) is provided so as to surround the projecting portion 63, between the support pedestal 61 and the Dewar vessel 50. As this packing is interposed between the support pedestal 61 and the Dewar vessel 50, watertightness is achieved between the support pedestal 61 and the Dewar vessel 50.

The support pedestal 61 is provided with a plurality of communicating passages 64 which are formed so as to establish communication between the predetermined gap G2 formed between the internal peripheral surface of the second case 43 and the external peripheral surface of the support pedestal 61, and the predetermined gap G3 formed between the second surface 61b of the support pedestal 61 and the Dewar vessel 50. The communicating passages 64 are arranged at equiangular intervals (e.g., at intervals of approximately 90°) around the center axis of the through hole 62. Each communicating passage 64 consists of a first passage portion 65 and a second passage portion 66. The first passage portion 65 opens on the external peripheral surface of the support pedestal 61 and extends in a radial direction of the support pedestal 61 from the external peripheral surface of the support pedestal 61. The second passage portion 66 extends in a direction parallel to the center axis of the through hole 62 from the first passage portion 65 and opens on the second surface 61b.

Predetermined gaps G4, G5, and G6 are formed between the external periphery of the second container portion 50b of the Dewar vessel 50 and the internal peripheral surface of the through hole 62 formed in the support pedestal 61, between the external periphery of the second container portion 50b and the internal peripheral surface of the opening 48 formed in the second lid plate 47, and between the external periphery of the second container portion 50b and the internal peripheral surface of the first sample introduction opening 23, respectively. The gaps G4, G5, and G6 communicate with each other and also communicate with the predetermined gap G3 between the second surface 61b of the support pedestal 61 and the Dewar vessel 50 and with the space in the integrating sphere 20. These cause the space in the Dewar vessel 50 to communicate with the space in the integrating sphere 20 through the plurality of communicating passages 64 formed in the support pedestal 61, the predetermined gap G3 formed between the second surface 61b of the support pedestal 61 and the Dewar vessel 50, the predetermined gap G4 formed between the external periphery of the second container portion 50b and the internal peripheral surface of the through hole 62, the predetermined gap G5 formed between the external periphery of the second container portion 50b and the internal peripheral surface of the opening 48 of the second lid plate 47, and the predetermined gap G6 formed between the external periphery of the second container portion 50b and the internal peripheral surface of the first sample introduction opening 23.

The length of the second container portion 50b is so set that the tip portion of the second container portion 50b projects by a predetermined length into the integrating sphere 20 in a state in which the Dewar vessel 50 is in contact with a contact surface of the support pedestal 61. Particularly, the length of the second container portion 50b is set so that the sample S held in the sample holder 80 positioned in the Dewar vessel 50 is located in the integrating sphere 20. This causes the tip portion of the second container portion 50b to be exposed in the integrating sphere 20.

The Dewar vessel 50 and the sample holder 80 are preferably made of a material that transmits light including the excitation light and the measured light, and a material suitably applicable herein is, for example, an optical cell made of synthetic silica glass.

The first sample introduction opening 23 and the sample holder 80 can be suitably used, for example, in the case where the sample S is a solution with a luminescence material being dissolved therein. This sample holder 80 can also be used where the sample S is a solid sample, a powder sample, or the like. The second sample introduction opening 24 and the sample holder 240 can be suitably used, for example, in the case where the sample S is a solid sample or a powder sample. In this case, the sample holder to be used is, for example, a sample holding substrate, a Petri dish, or the like.

The sample holders 80, 240 are used depending upon types of sample S, contents of spectrometry, and so on. When the sample holder 80 is used, the integrating sphere 20 is set in a state in which the ground contact surface 281 of the mount 280 faces down so as to keep the optical axis L along a horizontal line. When the sample holder 240 is used, the integrating sphere 20 is set in a state in which the ground contact surface 282 of the mount 280 faces down so as to keep the optical axis L along a vertical line. The following will describe a situation in which spectrometry of the sample S is carried out using the sample holder 80.

The light guide 13 for inputting of irradiation light is held in a state in which it is positioned by a light guide holding portion 211 of the light guide holder 210. The light from the irradiation light source 11 (cf. FIG. 1) is guided to the integrating sphere 20 by the light guide 13 and, while being collected by a condensing lens 212 in the light guide holder 210, it is radiated into the sample holder 80. In the present embodiment, the portion of the sample holder 80 holding the sample S is located at a position away from the optical path of excitation light from the entrance aperture 21. The light guide 25 for emission of measured light is held in a state in which it is positioned by the light guide holder 220.

When the excitation light of the predetermined wavelength is supplied as irradiation light from the irradiation light supplying section 10, light from the sample S irradiated with the excitation light is multiply diffusely reflected by the high diffuse reflection powder (e.g., Spectralon (registered trademark), barium sulfate, or the like) applied over the internal wall of the integrating sphere body 200. The diffusely reflected light is incident into the light guide 25 connected to the light guide holder 220, to be guided as measured light to the spectroscopic analyzer 30. In this way, spectrometry is carried out for the measured light from the sample S. The light from the sample S to be the measured light includes luminescence such as fluorescence produced in the sample S by irradiation with the excitation light, and the light component resulting from scattering, reflection, etc. of the excitation light by the sample S.

Figure 8:
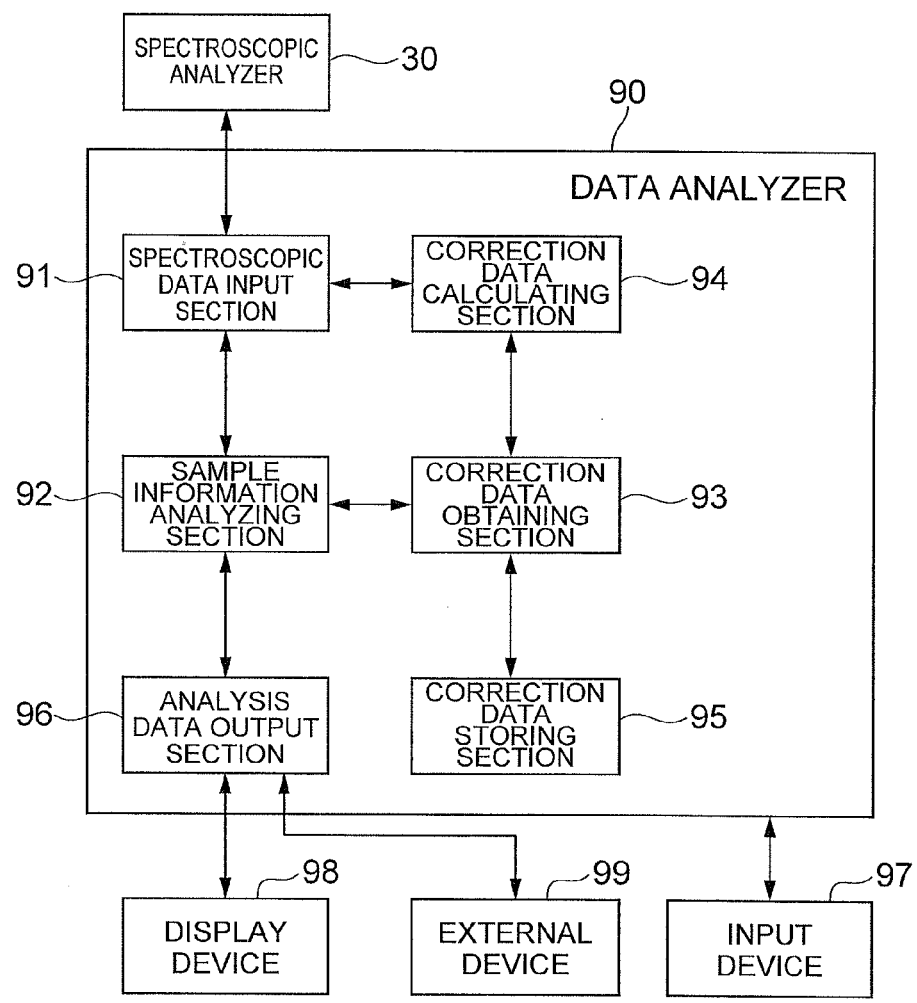
FIG. 8 is a block diagram showing an example of a configuration of a data analyzer.

FIG. 8 is a block diagram showing an example of the configuration of the data analyzer 90 used in the spectrometer 1A shown in FIG. 1. The data analyzer 90 in the present configuration example is configured with a spectroscopic data input section 91, a sample information analyzing section 92, a correction data obtaining section 93, and an analysis data output section 96. The data analyzer 90 is provided with a correction data calculating section 94 and a correction data storing section 95 in association with the correction data obtaining section 93.

The spectroscopic data input section 91 receives input of data such as a wavelength spectrum obtained as spectroscopic data by the spectroscopic analyzer 30. The spectroscopic data input section 91 functions as an input means. The spectroscopic data input through the spectroscopic data input section 91 is sent to the sample information analyzing section 92. The sample information analyzing section 92 analyzes the input wavelength spectrum to obtain information about the sample S. The sample information analyzing section 92 functions as a sample information analyzing means. The correction data obtaining section 93 obtains correction data for correction for the wavelength spectrum in view of light absorption by the sample holder 80, specifically, absorption of at least either the excitation light or luminescence from the sample S, for the aforementioned configuration wherein the sample S is held in the sample holder 80 in the integrating sphere 20. The correction data obtaining section 93 functions as a correction data obtaining means. The sample information analyzing section 92 corrects the wavelength spectrum with the correction data obtained by the correction data obtaining section 93 and analyzes the corrected wavelength spectrum to obtain information of the sample S such as a luminescence quantum yield by the PL method.

The correction data for the wavelength spectrum can be obtained, for example, from the correction data calculating section 94. The correction data calculating section 94 refers to the wavelength spectrum of the measurement result for derivation of the correction data executed under a predetermined condition and calculates the correction data, based thereon. The correction data calculating section 94 functions as a correction data calculating means. A specific calculation method of the correction data will be described below. If the correction data for the wavelength spectrum is preliminarily obtained, it is also possible to adopt a configuration wherein the correction data is stored in the correction data storing section 95 and wherein the correction data obtaining section 93 reads and obtains the correction data therefrom as occasion demands. In this case, the data analyzer may be configured without the correction data calculating section 94. The data analyzer may also employ a configuration wherein the correction data calculated by the correction data calculating section 94 is stored in the correction data storing section 95 and wherein the correction data obtaining section 93 reads the correction data as occasion demands.

The analysis data output section 96 outputs the analysis result of sample information resulting from the analysis by the sample information analyzing section 92. The analysis data output section 96 functions as an output means. When the data of the analysis result is fed to the display device 98 through the analysis data output section 96, the display device 98 displays the analysis result on a predetermined display screen for an operator. The recipient to receive the output of the analysis result is not always limited solely to the display device 98, but the data may be output to another device. FIG. 8 shows the configuration wherein an external device 99, in addition to the display device 98, is connected to the analysis data output section 96. Examples of the external device 99 include a printer, an external memory, other terminal equipment, and so on.

The spectrometer 1A shown in FIGS. 1 to 7 is configured employing the integrating sphere 20 provided with the aperture 21 for inputting of excitation light and the aperture 22 for emission of measured light and configured to enable the measurement of the luminescence properties of the sample S by the PL method, and the spectroscopic analyzer 30 which spectroscopically measures the measured light so as to allow distinguishment between the excitation light and the luminescence from the sample S by their wavelength spectra. For the sample holder 80 holding the sample S in the integrating sphere 20, the analyzer 90 prepares the correction data taking account of light absorption by the sample container, corrects the wavelength spectrum with this correction data, and then performs the analysis of the wavelength spectrum and the derivation of the sample information. This enables the spectrometry of the sample S to be suitably and accurately carried out, while suppressing error in the analysis result such as the luminescence quantum yield, even in the case where influence of absorption of light by the sample holder 80 is unignorable.

Figure 9:
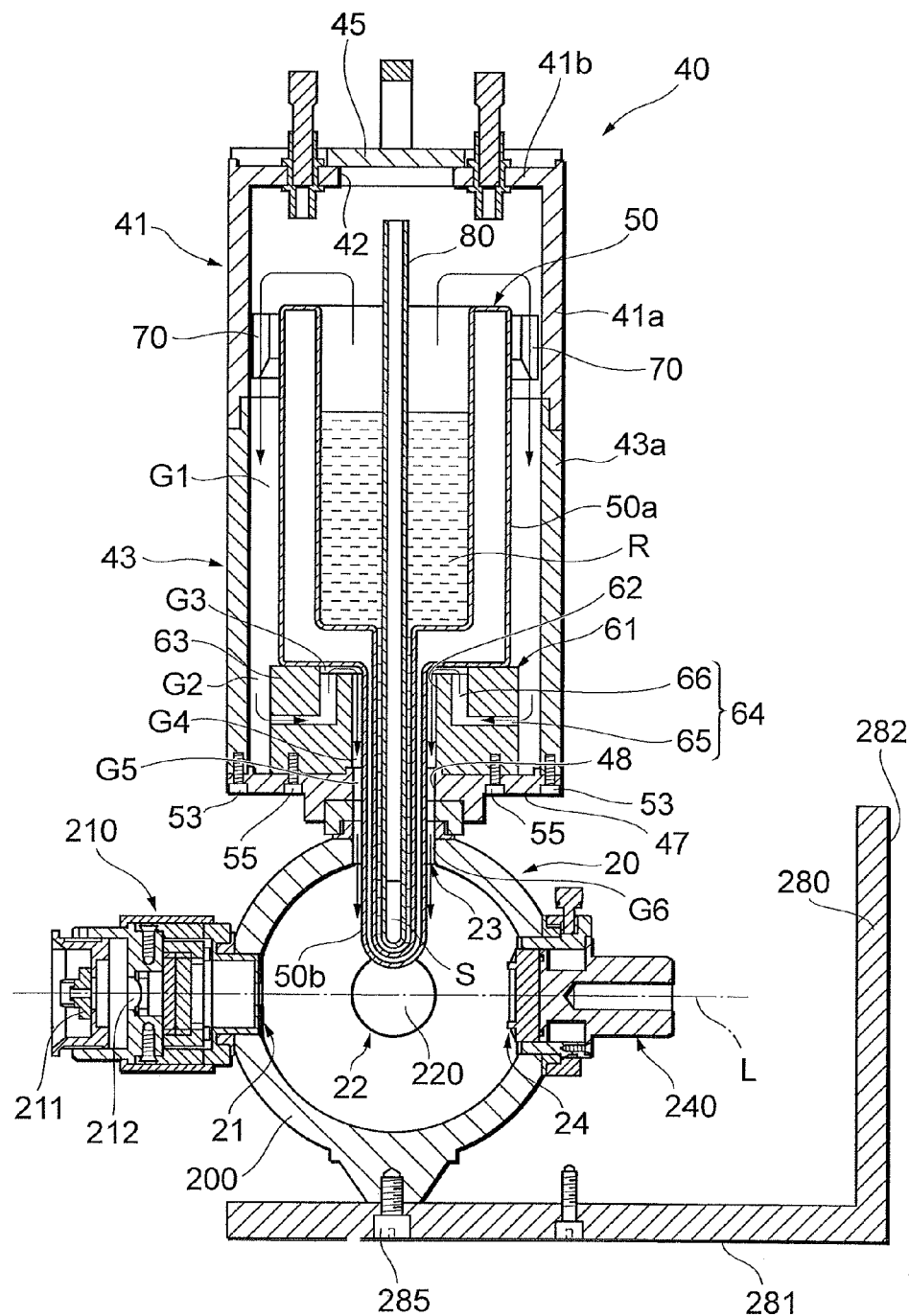
FIG. 9 is a perspective view showing an example of configurations of the integrating sphere, Dewar housing, and Dewar vessel.
Figure 10:
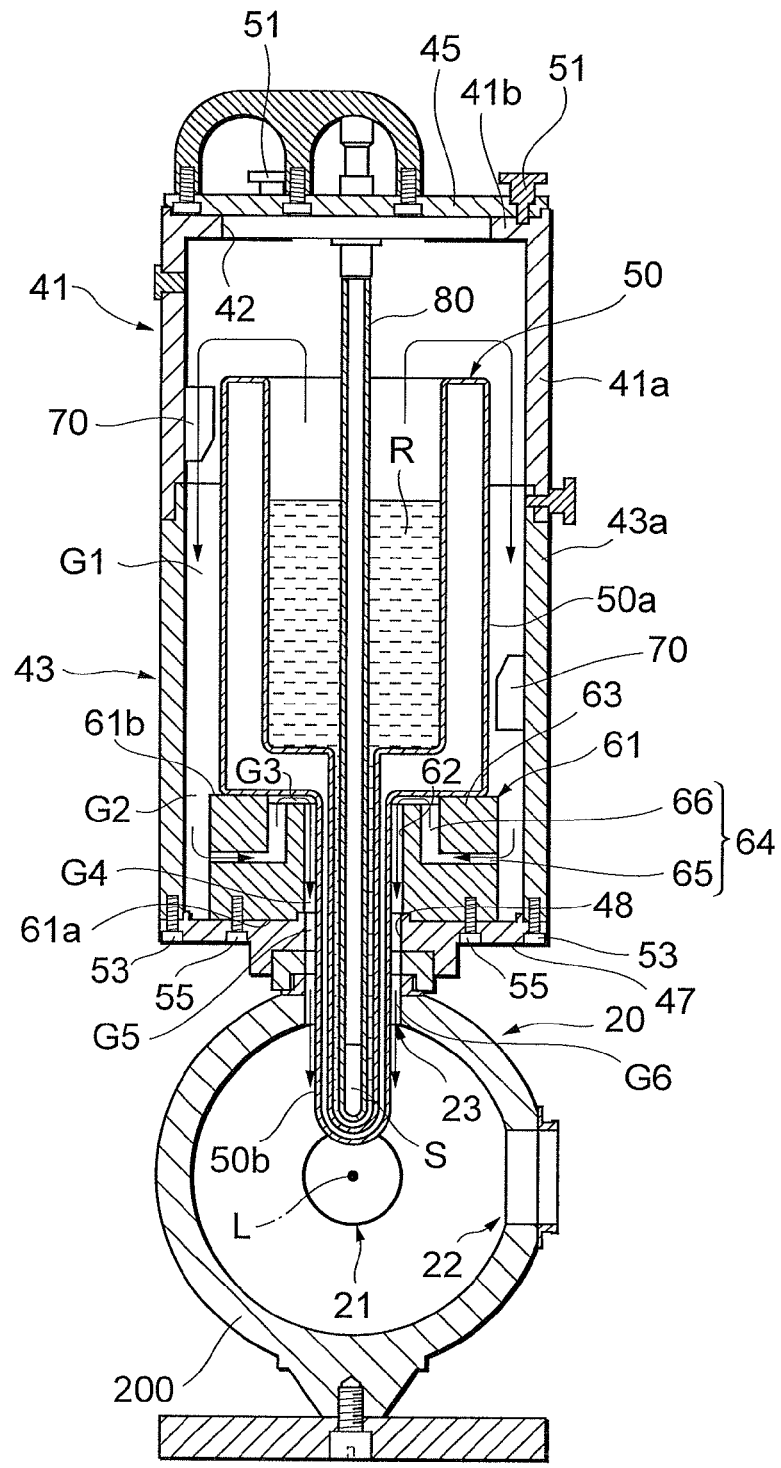
FIG. 10 is a perspective view showing an example of configurations of the integrating sphere, Dewar housing, and Dewar vessel.

Incidentally, the present embodiment allows the measurement in a state in which the sample S is cooled by the refrigerant R retained in the Dewar vessel 50, as shown in FIGS. 9 and 10. For example, if the refrigerant R is liquid nitrogen, the spectrometry of the sample S can be performed around the liquid nitrogen temperature (approximately $-196°$ C.). In this manner, since the present embodiment employs the Dewar vessel 50 retaining the refrigerant R, the sample S can be easily and efficiently cooled.

During the measurement, the refrigerant R retained in the Dewar vessel 50 vaporizes and vaporization of the refrigerant R results in generating relatively cool and dry gas. The gas generated from the refrigerant R, as indicated by arrows in FIGS. 9 and 10, is introduced into the integrating sphere 20 through the predetermined gap G1 formed between the internal peripheral surfaces of the first case 41 and the second case 43 and the external peripheral surface of the first container portion 50a, the predetermined gap G2 formed between the internal peripheral surface of the second case 43 and the external peripheral surface of the support pedestal 61, the plurality of communicating passages 64 formed in the support pedestal 61, the predetermined gap G3 formed between the second surface 61b of the support pedestal 61 and the Dewar vessel 50, the predetermined gap G4 formed between the external periphery of the second container portion 50b and the internal peripheral surface of the through hole 62, the predetermined gap G5 formed between the external periphery of the second container portion 50b and the internal peripheral surface of the opening 48 of the second lid plate 47, and the predetermined gap G6 formed between the external periphery of the second container portion 50b and the internal peripheral surface of the first sample introduction opening 23. Namely, the gaps G1-G6 and the communicating passages 64 function as a gas introduction path which introduces the gas generated from the refrigerant R retained in the Dewar vessel 50, into the integrating sphere 20. The gas introduced into the integrating sphere 20 absorbs water in the integrating sphere 20 to decrease the temperature in the integrating sphere 20.

In the present embodiment, therefore, the interior of the integrating sphere 20 is kept in a relatively cool and dry ambience by the gas generated from the refrigerant R, which can prevent dew condensation from occurring on the portion of the second container portion 50b of the Dewar vessel 50 exposed in the integrating sphere 20.

In the present embodiment, the gas generated from the refrigerant R flows through the predetermined gap G6 formed between the external periphery of the second container portion 50b and the first sample introduction opening 23, into the integrating sphere 20. The gas flowing into the integrating sphere 20 then flows along the portion of the second container portion 50b of the Dewar vessel 50 exposed in the integrating sphere 20. This gas flow actively lowers the ambient temperature and humidity near the portion of the second container portion 50b exposed in the integrating sphere 20. This allows more secure prevention of dew condensation on the portion of the second container portion 50b exposed in the integrating sphere 20.

The integrating sphere 20, basically, is constructed in a lightproof structure but there are small clearances to let gas pass, at the entrance aperture 21, the exit aperture 22, and so on. For this reason, the gas having absorbed water in the integrating sphere 20 is discharged through the small clearances existing at the entrance aperture 21, the exit aperture 22, etc. to the outside of the integrating sphere 20. Incidentally, the integrating sphere 20 may be provided with a separate discharge opening for discharging the gas having absorbed water in the integrating sphere 20, to the outside of the integrating sphere 20. In terms of the requirement for the lightproof structure of the integrating sphere 20, however, it is preferable to adopt the configuration wherein the gas is discharged through the aforementioned small clearances existing at the entrance aperture 21, the exit aperture 22, and so on.

In the present embodiment, as described above, the gas generated from the refrigerant R flows through the predetermined gap G1 formed between the internal peripheral surfaces of the first case 41 and the second case 43 and the external peripheral surface of the first container portion 50a, in the Dewar housing 40. This also lowers the ambient temperature and humidity near the external peripheral surface of the first container portion 50a, so as to prevent occurrence of dew condensation on the external peripheral surface of the first container portion 50a and others. Even if water condenses on the external peripheral surface of the first container portion 50a and others to be collected in the Dewar housing 40, the water is prevented from entering the interior of the integrating sphere 20 because the packings 71, 72 achieve water-tightness between the second lid plate 47 and the support pedestal 61 and between the support pedestal 61 and the Dewar vessel 50. Since each of the communicating passages 64 consists of the first passage portion 65 and the second passage portion 66, water is unlikely to pass through the communicating passages 64 to enter the integrating sphere 20. The water collected in the Dewar housing 40 is discharged from the drainage opening 49.

In the present embodiment, the Dewar housing 40 covers the first container portion 50a of the Dewar vessel 50 exposed from the integrating sphere 20. This prevents the gas generated from the refrigerant R from being dissipated to the outside of the apparatus whereby the gas can be efficiently guided into the integrating sphere 20. In the present embodiment, the Dewar housing 40 constitutes a portion of the aforementioned gas introduction path. This allows secure and easy installation of the foregoing gas introduction path.

The present embodiment comprises the sample holder 80 housing the sample S and disposed in the Dewar vessel 50. This permits the sample S to be surely cooled without contact with the refrigerant R.

The above described the preferred embodiment of the present invention, and it should be noted that the present invention is by no means intended to be limited to the foregoing embodiment but can be modified in various ways without departing from the spirit and scope of the invention.

The present embodiment is provided with the Dewar housing 40 housing the Dewar vessel 50, but the Dewar housing 40 is not always essential. If the spectrometer is configured without the Dewar housing 40, it may be so configured that the Dewar vessel 50 and the integrating sphere 20 are connected by a pipe or the like and that the gas generated from the refrigerant R is introduced through the pipe or the like into the integrating sphere 20.

In the present embodiment, the Dewar housing 40 and the integrating sphere 20 are connected through the plurality of communicating passages 64 formed in the support pedestal 61, the predetermined gap G3 formed between the second surface 61b of the support pedestal 61 and the Dewar vessel 50, the predetermined gap G4 formed between the external periphery of the second container portion 50b and the internal peripheral surface of the through hole 62, the predetermined gap G5 formed between the external periphery of the second container portion 50b and the internal peripheral surface of the opening 48 of the second lid plate 47, and the predetermined gap G6 formed between the external periphery of the second container portion 50b and the internal peripheral surface of the first sample introduction opening 23, but the communication way between them does not always have to be limited to it. The spectrometer may also be configured in such a manner that the Dewar housing 40 and the integrating sphere 20 are connected by a pipe or the like and the gas generated from the refrigerant R is introduced through the pipe or the like from the interior of the Dewar housing 40 into the integrating sphere 20.

Figure 11:
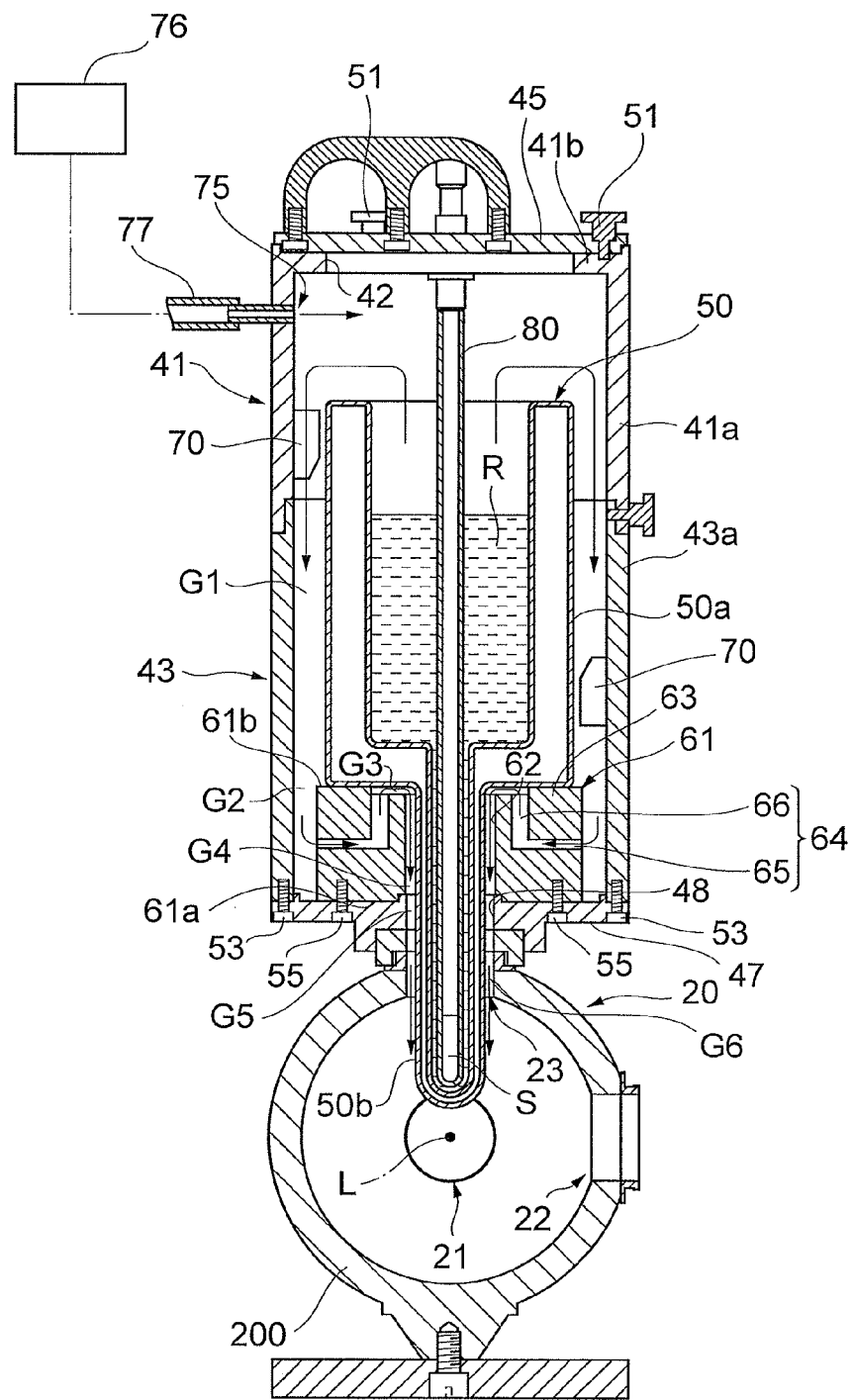
FIG. 11 is a perspective view showing an example of configurations of the integrating sphere, Dewar housing, and Dewar vessel.
Figure 12:
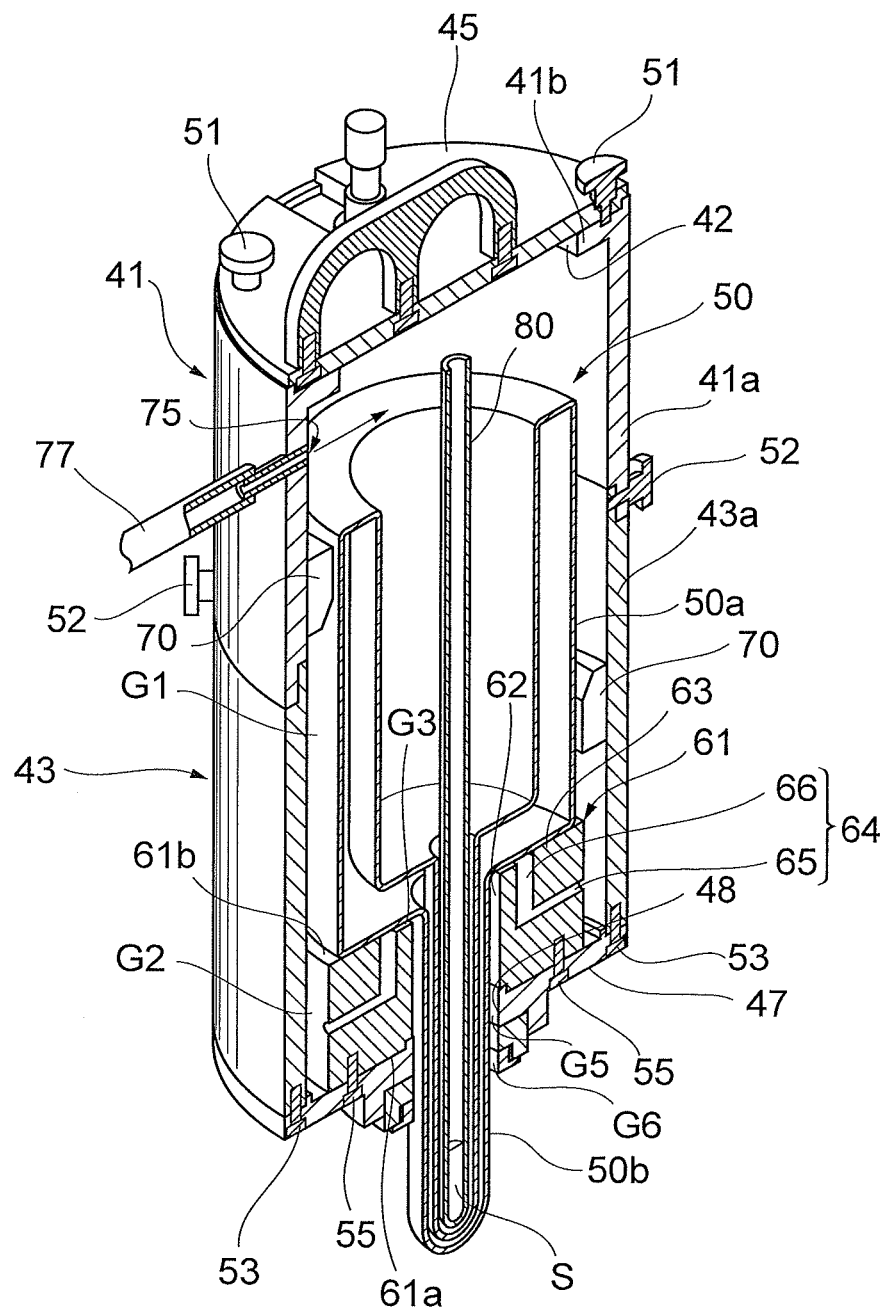
FIG. 12 is a perspective view showing an example of configurations of the integrating sphere, Dewar housing, and Dewar vessel.

The present embodiment adopts introduction of the gas generated by vaporization of the refrigerant R, into the integrating sphere 20, but it is also possible to adopt a way of introducing dry gas into the integrating sphere 20 along with the introduction of the generated gas. For example, a conceivable configuration is, as shown in FIGS. 11 and 12, such that the Dewar housing 40 (e.g., the first case 41) is provided with an introduction opening 75 for introducing dry gas thereinto and a gas passage 77 from a dry gas supply unit 76 is connected to the introduction opening 75. Namely, the gas introduction path for introducing the gas generated from the refrigerant R, into the integrating sphere 20 functions as a gas introduction path for introducing the dry gas into the integrating sphere 20. It is also possible to use separate paths as the gas introduction path for introducing the dry gas into the integrating sphere 20 and the gas introduction path for introducing the gas generated from the refrigerant R, into the integrating sphere 20, and to introduce the dry gas directly into the integrating sphere 20. The dry gas applicable herein is, for example, nitrogen gas, helium gas, and so on.

Figure 13:
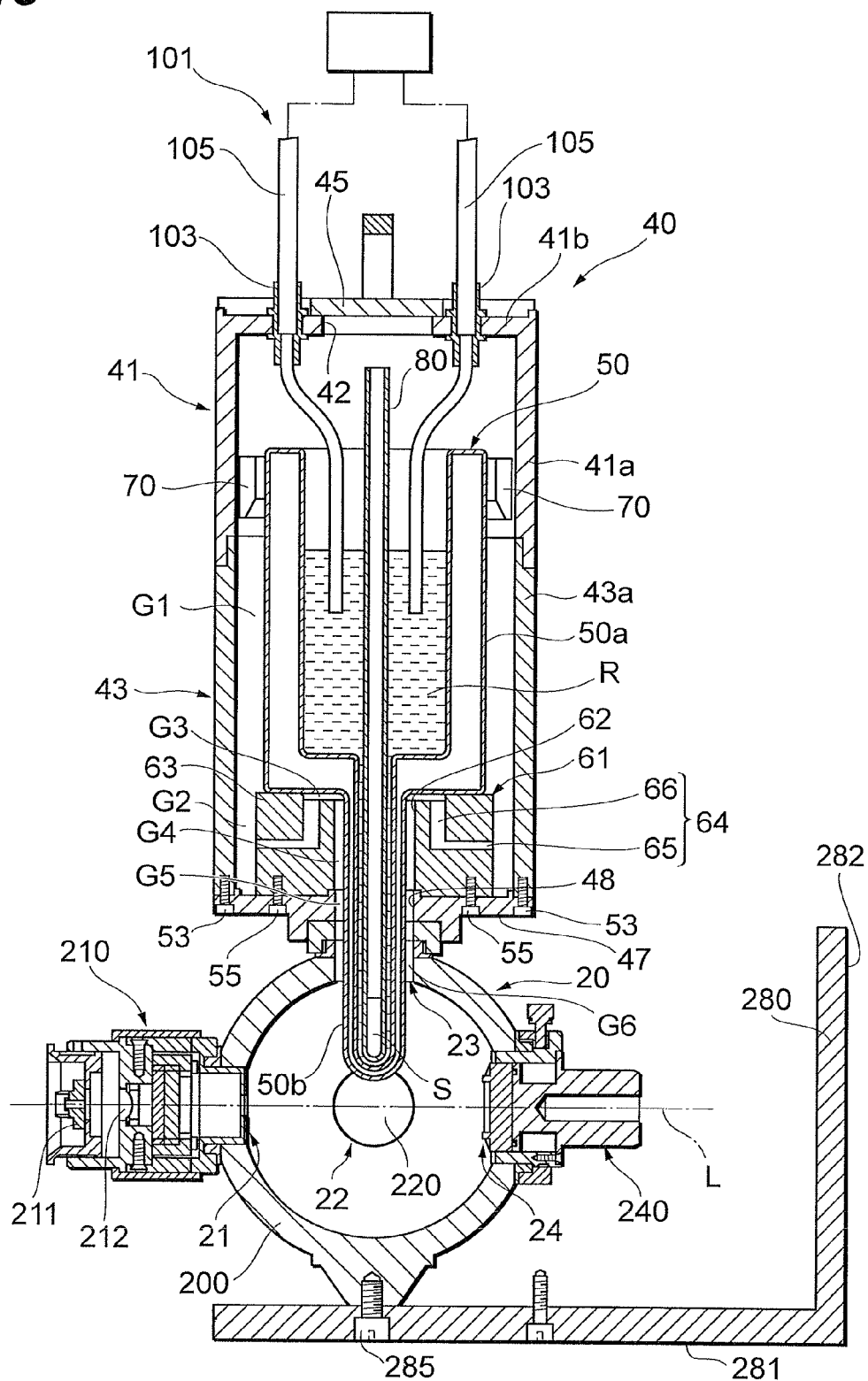
FIG. 13 is a perspective view showing an example of configurations of the integrating sphere, Dewar housing, and Dewar vessel.

In the present embodiment, as shown in FIG. 13, the temperature of the refrigerant R retained in the Dewar vessel 50 may be regulated by a chiller 101. In this case, the spectrometry of the sample S can be carried out at any temperature. Connection to the chiller 101 can be implemented by providing the Dewar housing 40 (e.g., the first case 41 and the first lid plate 45) with tube connectors 103 and connecting tubes 105 to the respective tube connectors 103.

Figure 14:
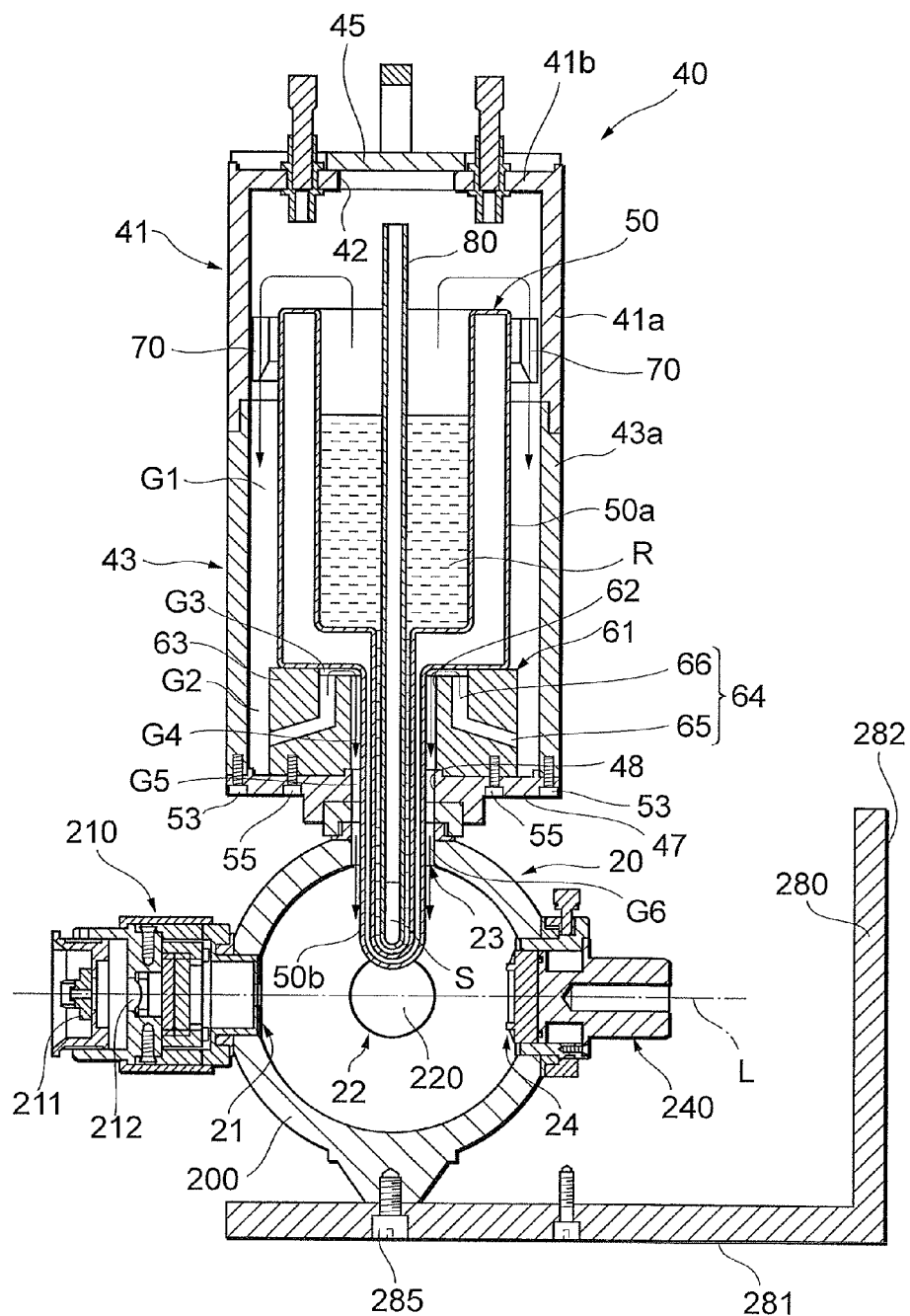
FIG. 14 is a perspective view showing an example of configurations of the integrating sphere, Dewar housing, and Dewar vessel.

The first passage portion 65 of each communicating passage 64 may be formed, as shown in FIG. 14, in such a manner that it is downwardly inclined from the connection portion to the second passage portion 66 toward the opening portion on the external peripheral surface of the support pedestal 61. In this case, water drops generated in the communicating passages 64 are likely to be discharged to the outside of the support pedestal 61. The second passage portions 66 do not always have to be formed so as to extend in the direction parallel to the center axis of the through hole 62, but may be formed as inclined relative to the direction parallel to the center axis of the through hole 62.

INDUSTRIAL APPLICABILITY

The present invention is applicable to the spectrometer configured to apply the excitation light of a predetermined wavelength to the sample and to measure and evaluate the luminescence properties such as the fluorescence property of the sample by the photoluminescence method.

REFERENCE SIGNS LIST 1A spectrometer; 20 integrating sphere; 21 entrance aperture; 22 exit aperture; 23 first sample introduction opening; 40

Dewar housing; 41 first case; 43 second case; 45 first lid plate; 47 second lid plate; 48 opening; 50 Dewar vessel; 61 support pedestal; 62 through hole; 64 communicating passages; 80 sample holder; G1-G6 gaps; R refrigerant; S sample.

The invention claimed is:

1. A spectrometer comprising an optical element inside which a sample of a measurement target is disposed and which is adapted for observing measured light emitted from the sample, the optical element has an internal surface defining an integrating space, the internal surface is covered with a high diffuse reflection material, said spectrometer comprising:
   a Dewar vessel which retains a refrigerant for cooling the sample and at least a portion of which is arranged in the integrating space; and
   a gas introduction path which introduces gas generated from the refrigerant retained in the Dewar vessel, to the integrating space,
   wherein a gap between the optical element and the Dewar vessel constitutes the gas introduction path.

2. The spectrometer according to claim 1, further comprising a cover which covers a portion of the Dewar vessel exposed out of the optical element.

3. The spectrometer according to claim 2, wherein the cover is provided with the gas introduction path.

4. The spectrometer according to claim 1, further comprising a sample holder which houses the sample and which is disposed in the Dewar vessel.

5. The spectrometer according to claim 1, further comprising a gas introduction path which introduces dry gas to the integrating space.

6. The spectrometer according to claim 1,
   wherein the Dewar vessel is a nearly tubular container closed at one end and is constructed in a heat-insulated double structure with a vacuum layer, the Dewar vessel has a first container portion having a first inside diameter and located on the other end side, and a second container portion having a second inside diameter smaller than the first inside diameter and located on one end side.

7. The spectrometer according to claim 6,
   wherein a tip portion of the second container portion projects into the integrating space.

8. The spectrometer according to claim 6, further comprising:
   a Dewar housing having a first and a second cases and having a space for housing the Dewar vessel inside,
   wherein the Dewar vessel is radially positioned by a plurality of spacers disposed at predetermined intervals on internal peripheral surfaces of the first and the second cases, the spacers form a predetermined first gap between the internal peripheral surfaces of the first and the second cases and an external peripheral surface of the first container portion.

9. The spectrometer according to claim 8, further comprising:
   a support pedestal supporting the Dewar vessel, and
   wherein the Dewar housing further has a first lid plate detachably attached to a bottom portion of the first case and a second lid plate detachably attached to one end of the second case,
   wherein the support pedestal is detachably attached to the second lid plate, and
   wherein the support pedestal is provided with a projecting portion projecting from a second surface, on the second surface opposed to a first surface attached to the second lid plate.

10. The spectrometer according to claim 9,
    wherein the projecting portion is in contact with the Dewar vessel to define a position of the Dewar vessel in an insertion direction thereof.

11. The spectrometer according to claim 10,
    wherein the second surface of the support pedestal and the Dewar vessel are separated by a distance of a height of the projecting portion to form a predetermined second gap between the second surface of the support pedestal and the Dewar vessel.

12. The spectrometer according to claim 11,
    wherein a predetermined third gap is formed between the internal peripheral surface of the second case and the external peripheral surface of the support pedestal, and
    wherein the support pedestal is provided with a plurality of communicating passages which are formed so as to establish communication between the predetermined second gap and the predetermined third gap.

13. The spectrometer according to claim 9,
    wherein the optical element is provided with a sample introduction opening configured to introduce the sample into the integrating space,
    wherein an opening for insertion of the second container portion is formed in a central region of the second lid plate so as to communicate with the sample introduction opening,
    wherein a through hole for insertion of the second container portion is formed in a central portion of the support pedestal so as to communicate with the opening formed in the second lid plate, and
    wherein predetermined fourth, fifth, and sixth gaps are formed between the external periphery of the second container portion and the internal peripheral surface of the through hole formed in the support pedestal, between the external periphery of the second container portion and the internal peripheral surface of the opening formed in the second lid plate, and between the external periphery of the second container portion and the internal peripheral surface of the sample introduction opening, respectively.

14. The spectrometer according to claim 13,
    wherein the predetermined fourth, fifth, and sixth gaps communicate with each other and also communicate with the predetermined second gap and the integrating space.

15. The spectrometer according to claim 4,
    wherein the sample holder is a tubular member closed at one end.

16. The spectrometer according to claim 15,
    wherein the Dewar vessel has a first container portion having a first inside diameter and located on the other end side, and a second container portion having a second inside diameter smaller than the first inside diameter and located on one end side, and
    wherein the second inside diameter is set larger than an outside diameter of the sample holder.

17. The spectrometer according to claim 16,
    wherein the optical element is provided with a sample introduction opening configured to introduce the sample into the integrating space, at least the portion of the Dewar vessel is inserted into the sample introduction opening,
    wherein a gap between the Dewar vessel and the internal peripheral surface of the sample introduction opening constitutes the gas introduction path.

18. The spectrometer according to claim 1,
    wherein the optical element is an integrating sphere.

19. A spectrometer comprising an optical element inside which a sample of a measurement target is disposed and which is adapted for observing measured light emitted from the sample, the optical element has an internal surface defining an integrating space, the internal surface is covered with a high diffuse reflection material, said spectrometer comprising:
- a Dewar vessel which retains a refrigerant for cooling the sample and at least a portion of which is arranged in the integrating space; and
- a gas introduction path which introduces dry gas to the integrating space,
- wherein a gap between the optical element and the Dewar vessel constitutes the gas introduction path.

* * * * *